(12) United States Patent
Davis et al.

(10) Patent No.: US 7,211,884 B1
(45) Date of Patent: May 1, 2007

(54) IMPLANTABLE MEDICAL DEVICE CONSTRUCTION USING A FLEXIBLE SUBSTRATE

(75) Inventors: Dion F. Davis, Palmdale, CA (US); Gabriel A. Mouchawar, Valencia, CA (US); Alvin H. Weinberg, Moorpark, CA (US)

(73) Assignee: Pacesetter, Inc., Sylmar, CA (US)

( * ) Notice: Subject to any disclaimer, the term of this patent is extended or adjusted under 35 U.S.C. 154(b) by 703 days.

(21) Appl. No.: 10/059,739

(22) Filed: Jan. 28, 2002

(51) Int. Cl.
   *H01L 23/02* (2006.01)
(52) U.S. Cl. .................. 257/685; 257/723; 257/730; 257/784
(58) Field of Classification Search ............. 257/685, 257/686, 723, 787, 790–793, 773, 789, 730, 257/704, 706, 784, 786
   See application file for complete search history.

(56) References Cited

U.S. PATENT DOCUMENTS

| | | | |
|---|---|---|---|
| 3,262,023 A | 7/1966 | Boyle | 317/101 |
| 3,904,934 A | 9/1975 | Martin | 317/101 |
| 4,082,394 A | 4/1978 | Gedney et al. | 339/17 |
| 4,192,565 A | 3/1980 | Gianni | 339/17 |
| 4,249,196 A | 2/1981 | Durney et al. | 357/74 |
| 4,288,841 A | 9/1981 | Gogal | 361/414 |
| 4,399,819 A | 8/1983 | Cowdery | 128/419 |
| 4,445,274 A | 5/1984 | Suzuki et al. | 29/832 |
| 4,467,400 A | 8/1984 | Stopper | 361/403 |
| 4,504,850 A | 3/1985 | Pollard et al. | 357/79 |
| 4,567,643 A | 2/1986 | Droguet et al. | 29/575 |
| 4,614,194 A | 9/1986 | Jones et al. | 128/419 |
| 4,616,655 A | 10/1986 | Weinberg et al. | 128/419 |
| 4,663,649 A | 5/1987 | Suzuki et al. | 357/67 |
| 4,714,981 A | 12/1987 | Gordon | 361/400 |
| 4,760,335 A | 7/1988 | Lindberg | 324/158 |

(Continued)

FOREIGN PATENT DOCUMENTS

JP   53-39891   12/1978

(Continued)

OTHER PUBLICATIONS

Weinberg, A., "Medical Microelectronic Packaging Using Low-Temperature Cofired Ceramics," ISHM's 1st Joint Technology Conference (JTC) San Diego, CA Mar. 26-28, 1990.

(Continued)

*Primary Examiner*—Hoai Pham
*Assistant Examiner*—DiLinh Nguyen

(57) ABSTRACT

A high density electronic circuit for use in an implantable stimulation device that comprises a flexible substrate that has the advantage of integrating "chip-and-wire" microelectronic circuits and flexible interconnections that are adapted to conform to the body compatible housing into a single structure. The flexible substrate has die attach pads, each die attach pad having a set of wire bond pads therearound, each wire bond pad being connected to conductors formed within the substrate according to circuit function. A plurality of chip-and-wire integrated circuit (IC) chips are mounted by epoxy die attachment on the die attach pads, each IC chip has a plurality of contact pads formed on a top surface thereof, and gold wire bonds electrically connect the plurality of contact pads to the wire bonds pads. The wire bonds include a primary bond and, optionally, a safety bond for reinforcement. Other techniques are disclosed to enable the use of the gold wire bonds on a flexible substrate.

20 Claims, 5 Drawing Sheets

U.S. PATENT DOCUMENTS

| | | | | |
|---|---|---|---|---|
| 4,763,188 A | 8/1988 | Johnson | | 357/74 |
| 4,766,481 A | 8/1988 | Gobrecht et al. | | 357/80 |
| 4,791,075 A | 12/1988 | Lin | | 437/209 |
| 4,807,021 A | 2/1989 | Okumura | | 357/75 |
| 4,833,102 A | 5/1989 | Byrne et al. | | 437/218 |
| 4,868,712 A | 9/1989 | Woodman | | 361/388 |
| 4,882,657 A | 11/1989 | Braun | | 361/412 |
| 4,959,749 A | 9/1990 | Dzarnoski, Jr. et al. | | 361/396 |
| 5,012,323 A | 4/1991 | Farnworth | | 357/75 |
| 5,028,986 A | 7/1991 | Sugano et al. | | 357/75 |
| 5,060,027 A | 10/1991 | Hart et al. | | 357/17 |
| 5,140,496 A | 8/1992 | Heinks et al. | | 361/306 |
| 5,144,946 A | 9/1992 | Weinberg et al. | | 178/419 |
| 5,208,782 A | 5/1993 | Sakuta et al. | | 365/203.03 |
| 5,291,061 A | 3/1994 | Ball | | 257/686 |
| 5,309,020 A | 5/1994 | Murasawa et al. | | 257/685 |
| 5,323,060 A | 6/1994 | Fogal et al. | | 257/777 |
| 5,330,504 A | 7/1994 | Somerville et al. | | 607/5 |
| 5,362,656 A | 11/1994 | McMahon | | 437/21 |
| 5,386,341 A | 1/1995 | Olson et al. | | 361/749 |
| 5,406,027 A | 4/1995 | Matsumoto et al. | | 174/52.2 |
| 5,422,435 A | 6/1995 | Takiar et al. | | 174/52.4 |
| 5,439,482 A | 8/1995 | Adams et al. | | 607/5 |
| 5,470,345 A | 11/1995 | Hassler et al. | | 607/36 |
| 5,473,198 A | 12/1995 | Hagiya et al. | | 257/786 |
| 5,674,260 A | 10/1997 | Weinberg | | 607/36 |
| 5,856,915 A | 1/1999 | Weinberg | | 361/790 |
| 5,931,764 A | 8/1999 | Freeman et al. | | 482/4 |
| 6,026,325 A | 2/2000 | Weinberg et al. | | 607/36 |
| 6,164,523 A * | 12/2000 | Fauty et al. | | 228/180.5 |
| 6,208,521 B1 * | 3/2001 | Nakatsuka | | 361/749 |
| 6,245,092 B1 | 6/2001 | Schaldach, Jr. | | 607/1 |
| 6,266,197 B1 * | 7/2001 | Glenn et al. | | 359/819 |
| 6,307,751 B1 | 10/2001 | Bodony et al. | | 361/790 |
| 6,324,428 B1 | 11/2001 | Weinberg et al. | | 607/36 |
| 6,541,867 B1 * | 4/2003 | Fjelstad | | 257/773 |
| 6,777,819 B2 * | 8/2004 | Huang | | 257/796 |

FOREIGN PATENT DOCUMENTS

| | | |
|---|---|---|
| JP | 55-61046 | 5/1980 |
| JP | 56-40268 | 4/1981 |
| JP | 58-92230 | 6/1983 |
| JP | 59-44851 | 3/1984 |
| JP | 59-44852 | 3/1984 |
| JP | 60-10764 | 1/1985 |
| JP | 60-38844 | 2/1985 |
| JP | 60-117763 | 6/1985 |
| JP | 60-182731 | 9/1985 |
| JP | 62-260353 | 12/1987 |
| JP | 63-128736 | 6/1988 |
| JP | 1-28855 | 1/1989 |
| JP | 1-44056 | 2/1989 |
| JP | 1-89356 | 4/1989 |
| JP | 1-147850 | 6/1989 |
| JP | 1-286353 | 11/1989 |
| JP | 2-146792 | 6/1990 |
| JP | 3-169062 | 7/1991 |
| JP | 4-56262 | 2/1992 |
| JP | 5-13663 | 1/1993 |
| WO | WO92/15368 | 9/1992 |

OTHER PUBLICATIONS

Weinberg, A., "Vertically Integrated Packaging of High Reliability Electronics," ISHM's 10th Southern California Regional Symposium & Exhibition, Los Angeles, CA May 8, 1990.

McAtee, D.J., Dual-In-Line Package Socket 'Piggyback' Structure IBM Technical Disclosure Bulletin, vol. 16, Mo. Sep. 1973.

Weinberg, A., "High Density Electronic Packaging Utilizing Vertical Integration and Low Temperature Co-fired Ceramics," ISHM '90 Proceedings.

Weinberg, A. et al., "High-Density, Double-Sided SMT Packaging of Vertically Integrated Chip Carriers for Cardiac Pacemakers," ISHM '88 Proceedings.

Jones, W.K. et al., "Circuit Interconnect Optimization Through the Use of A High Density Dual Cavity Ceramic Chip Carrier," ISHM '87 Proceedings.

Weingberg, A. et al., Vertically-Integrated Package, 1988 Proceedings, 38th Electronic Components Conference, May 9-11, 1988.

Tuckerman, D.B. et al., "Laminated Memory: A New 3-Dimensional Packaging Technology for MCM's," 1994 IEEE.

"8 Megabit High Speed CMOS SRAM (DPS512×16Mkn3)," Dense-Pac Microsystems, pp. 1-8, Revision D, no date.

Slide Presentation entitled "Technology Selection," Y890297.PS, Nov. 20, 1989.

* cited by examiner

IMPLANTABLE MEDICAL DEVICE CONSTRUCTION USING A FLEXIBLE SUBSTRATE

FIELD OF THE INVENTION

The present invention relates generally to implantable medical devices, such as implantable cardiac pacemakers, cardioverters, defibrillators, infusion pumps, and the like, and more particularly to a complex implantable medical device that utilizes a flexible substrate as the main chip-carrying substrate and that requires a very high density construction for a plurality of integrated circuit chips.

BACKGROUND OF THE INVENTION

Although the present invention will be described with particular reference to implantable cardioverters-defibrillators, it is to be appreciated that the invention has applications with respect to high density electronic component packaging for many other applications that require ultra-high density and high reliability in a small package.

Modern ICD's, for example, are designed to be implanted into the human body to provide pacing stimulation pulses and high voltage shocks to the heart. Such ICD's typically include a hermetically sealed housing which contains electronic circuitry for generating the needed therapy, high voltage capacitors, and a power source. Signals into and out of the circuitry are coupled through the housing by means of feedthrough terminals which, in turn, are coupled to implantable stimulation leads.

Modern ICD's have reached a high level of sophistication relative to their ability to improve the quality of life. Current research is focused on developing "smart" units capable of providing rate responsive pacing, in addition to, electrogram storage, enhanced diagnostics and four-chamber stimulation. The electronics typically include a microprocessor, memory chips such as RAM and ROM devices, and other associated active analog and digital components, together with numerous passive components, such as capacitors and resistors. It has been common in packaging such electronic circuitry to mount the assorted active and passive components onto a rigid microelectronic substrate or printed circuit board. As efforts proceed to design these advanced biomedical devices, a constant goal of reduced product size is continuously challenged by increases in circuit complexity.

There are several key factors which dictate technology selection for packaging the electronic circuitry for implantable biomedical products. The most important prerequisite is high reliability. Pacemaker electronics are designed and tested for 99 percent survival at a 90 percent confidence level for the projected product life, which is estimated to last a minimum of five years or longer from the date of implantation. Electrical performance must also be optimized for both the particular application desired and the overall power consumption.

Reduction in ICD size translates to a smaller incision in the patient and a lighter device, in general. Battery area accounts for roughly 20% of the total ICD size, the high voltage capacitors comprise about 20%, the connector top comprises about 10%, and the electronic circuitry package comprises the remaining 50%. The electronic package is the only area, at the present time, which has the flexibility to be designed to maximize component density. Consequently, double-sided multi-layer microelectronic substrate designs are quite typical.

Typical substrate technologies which meet the above criteria to varying degrees are printed circuit boards, conventional thick film substrates, and high temperature cofired ceramic substrates. However, each of these technologies possess limitations in meeting the design objectives for today's sophisticated ICD.

Printed circuit board approaches are clearly limited in packaging density when compared to thick film or cofired substrate designs.

While conventional thick film substrates have a high reliability rate, it affords only modest packaging density, suffers from poor layer to layer dielectric isolation (resulting in a higher incidence of crosstalk between conductors), and surface planarity may suffer in multilayer designs.

Conventional high density electronic circuits are customarily based on rigid ceramic substrates. So as to increase the packaging density of the components, their size can be reduced and bonding can be performed in as space-saving a manner as possible. The disadvantage of these cofired ceramic packages is that they are limited by high conductor trace resistance and poor dimensional control.

Current ICD packaging designs have several additional shortcomings that prevent them from significantly reducing their weight, volume, density and interconnectivity with other parts of the assembly that future ICDs will demand.

First, the high voltage requirements of an ICD necessitate that the interconnect substrate have a high dielectric strength. Suitable materials typically used are low-temp or high-temp co-fired ceramics. These ceramic substrates are composed of several layers, each typically 6 mils thick, and fairly heavy compared to other laminate technologies (for example, polyimide flex circuits, PCBs, and the like). Ceramic design rules require a routing density limited to 4 mil lines and spaces. Thus, the more complex the circuit design is, the more layers that are required for interconnect, and consequently the heavier the overall device that will result.

Secondly, ceramics require tungsten conductors deposited on each layer. The exposed conductors are plated with a layer of nickel followed by a layer of gold because gold does not attach directly to tungsten. It is to the last layer of gold that components are attached and electrically connected with wire bonds. Tungsten, which has an electrical resistivity three times that of copper, requires the high voltage charging components and outputs that carry high currents to be constructed from copper conductor on a PCB or a polyimide flex. Therefore, the use of a ceramic hybrid substrate necessitates the use of additional interconnect mechanisms to connect the ceramic hybrids to PCBs and to the outputs of the device.

These interconnect techniques increase the cost and volume of the ICD. They also reduce the ease of manufacturing and increase the complexity of the ICD, and ultimately result in a thicker and heavier device thereby reducing patient comfort.

Another interconnect material currently in use in implantable devices is "flexible polyimide", or "flex", circuits. Historically, flex circuits have been used in pacemakers and ICD's for flexible interconnection between a main hybrid substrate and the connections needed at various angles to the device feedthroughs, telemetry coils and battery connections, etc. Current assembly technology for complex multi-chip modules, such as for an ICD, on flexible polyimide substrates has been limited to surface-mounting of passive components or "flip-chips", (i.e., IC's that are mounted with their active side facing the substrate and attached using solder bumps).

However, surface-mounting of flip-chips is not compatible with the current commonly-used diodes, power transistors and integrated circuit (IC) chip set, because they require connections to the top and back of the die using wire bonds. Thus, in order to meet the current IC chip set and interconnect density, the optimum ICD substrate must be capable of wire bond attachment, partly because chip-and-wire mounting of components offers a very high packaging density versus conventional surface mounted components, and partly because of the availability and ease of manufacture of face-up bonded chip devices. "Chip-and-wire" may be defined as hybrid technology employing exclusively face-up-bonded chip devices, interconnected to the substrate conventionally by "flying" wires, that is, wire bonds.

It was in this context that the inventors investigated, "flexible polyimide", or "flex", circuits for its suitability as a primary substrate for mounting chip-and-wire integrated circuits for extremely complex multi-chip VLSI circuits. Flexible polyimide exhibits several advantages that make it attractive for an ICD substrate.

More specifically, flexible polyimide as a primary substrate has a reduced thickness and weight. The substrate can be made from ~3 mil layers, which translates to a 50% reduction in thickness and 500% lighter assembly, and it has a higher routing density, typically, capable of 2 mil lines and spaces (twice the density of ceramics).

A flexible polyimide substrate further has a lower conductor resistance since it uses copper conductors ($1.67 \times 10^6$ ohms-cm) compared to tungsten ($5.5 \times 10^6$ ohms-cm). The use of flexible substrates eliminate the need for additional PCB's or other polyimide flexible interconnection for interfacing with the high voltage charging components and outputs that carry high currents.

And finally, a flexible polyimide substrate is capable of integrating other interconnections. That is, a flexible polyimide substrate integrates the functionality of a conventional rigid hybrid circuit with a conventional flex circuit to thereby interconnect the feedthroughs, battery, telemetry coil, transformers, etc. into a single component.

Unfortunately, the problem with flexible polyimide is that it tends to move during wire bonding, thereby dissipating the energy, which tends to weaken the wire bond at the wire bond pad. The conventional fixture for holding substrates during wire bonding has multiple vacuum holes that when bonding one or two bonds, can be located away from the wire bond pad, but when bonding numerous of wire bonds in close proximity of each other, as is typical in an ICD design, the vacuum holes create a very non-uniform surface that provides more opportunity to let the flexible substrate move and dissipate the energy. Because the requirements for a typical ICD includes several VLSI integrated circuits (e.g., three or more of micro-processors, RAM, ROM, I/O chips, high voltage converters, etc.) and literally hundreds of wire bonds in close proximity to one another, it is necessary to have a technique and/or substrate construction that ensures that all the wire bonds are reliable without the need to test each one.

Additionally, the final assembly must be protected from handling damage and moisture that might result in the hermetically sealed housing.

What is required is a system that affords all the advantages of the flexible polyimide with an interconnect scheme that has the interconnect density and manufacturing flexibility of wire bonding approaches.

SUMMARY OF THE INVENTION

A high density electronic circuit is provided for use in an implantable stimulation device that comprises a flexible substrate that has the advantage of integrating "chip-and-wire" microelectronic circuits and flexible interconnections that are adapted to conform to the body compatible housing into a single structure.

The flexible substrate has die attach pads, each die attach pad having a set of wire bond pads therearound, each wire bond pad being connected to conductors formed within the substrate according to circuit function. A plurality of chip-and-wire integrated circuit (IC) chips are mounted by epoxy die attachment on the die attach pads, each IC chip has a plurality of contact pads formed on a top surface thereof, and wire bonds electrically connect the plurality of contact pads to the wire bonds pads.

To meet reliability standards for implantable devices, the VLSI require that the plurality of wire bonds use 1–1.25 mil gold wire with a predetermined amount of additional gold plating on the substrate wire bond pads on orders of magnitude above and beyond the conventional 1–3 micro-inches that is customarily done on flexible circuits. The predetermined amount of gold plating on the wire bonds pads must have a sufficient thickness to reliably adhere to the gold wire bonds during the wire bonding processing (e.g., it has been found that about 50 micro-inches of gold plating meets this criteria). It has also been found that electrolytic pattern-plating is the process that currently best achieves this level of additional gold plating on the wire bond pads. The gold wire bonds include a primary bond between the wire bond pad and the integrated circuit chip and, optionally, may include a safety bond for reinforcement.

The implantable device may also utilize heavy aluminum wires (about 8 mil) for the high voltage, high current conductors with at least about 1–3 micro-inches of gold plating, but generally (for the convenience of minimizing the number of processing steps) will use the same predetermined amount of gold as used with the wire bond pads for the gold wire bonds (e.g., 50 micro-inches).

For all of the advantages mentioned above, processes and substrate design specifications have been developed to enable the next generation of complex ICD's to be built using the combination of a flexible polyimide substrate with wire bond techniques. It has been discovered that there are a few key design and processing techniques that will work successfully together to the desired end: gold wire bonds for the VLSI chips, a predetermined amount of the gold plating is necessary on the wire bond pads to enable gold wire bonding; and a manufacturing tool was designed having a flat surface with sufficient porosity to pull enough vacuum to hold the substrate during wire bonding to limit movement of the target. Optionally, the wire bond pads may be structurally supported by routing an area of metallization in the layer immediately below the wire bond pads.

After wire bonding, a suitable encapsulant may be used to protect the microelectronics mechanically during final assembly and from moisture.

Advantageously, the output feedthroughs and the battery connections are connected directly to the flexible substrate. In addition, other components that are specific to the particular device, for example an ICD, may also be attached directly to the flexible substrate, such as one or more high voltage capacitors, additional sensors, and a transformer. Therefore, an ICD is assembled in this manner would require no additional interconnect mechanisms.

The end result of the technique of this invention is an ICD which is thinner and lighter, more reliable, easier to manufacture, and is lower in cost. To apply some numbers to these statements, the weight of an LCD embodying this technology can be reduced by about 17%.

BRIEF DESCRIPTION OF THE DRAWINGS

The above and further features, advantages and benefits of the present invention will be apparent upon consideration of the following detailed description, taken in conjunction with the accompanying drawings, in which like reference characters refer to like parts throughout, and in which.

DETAILED DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
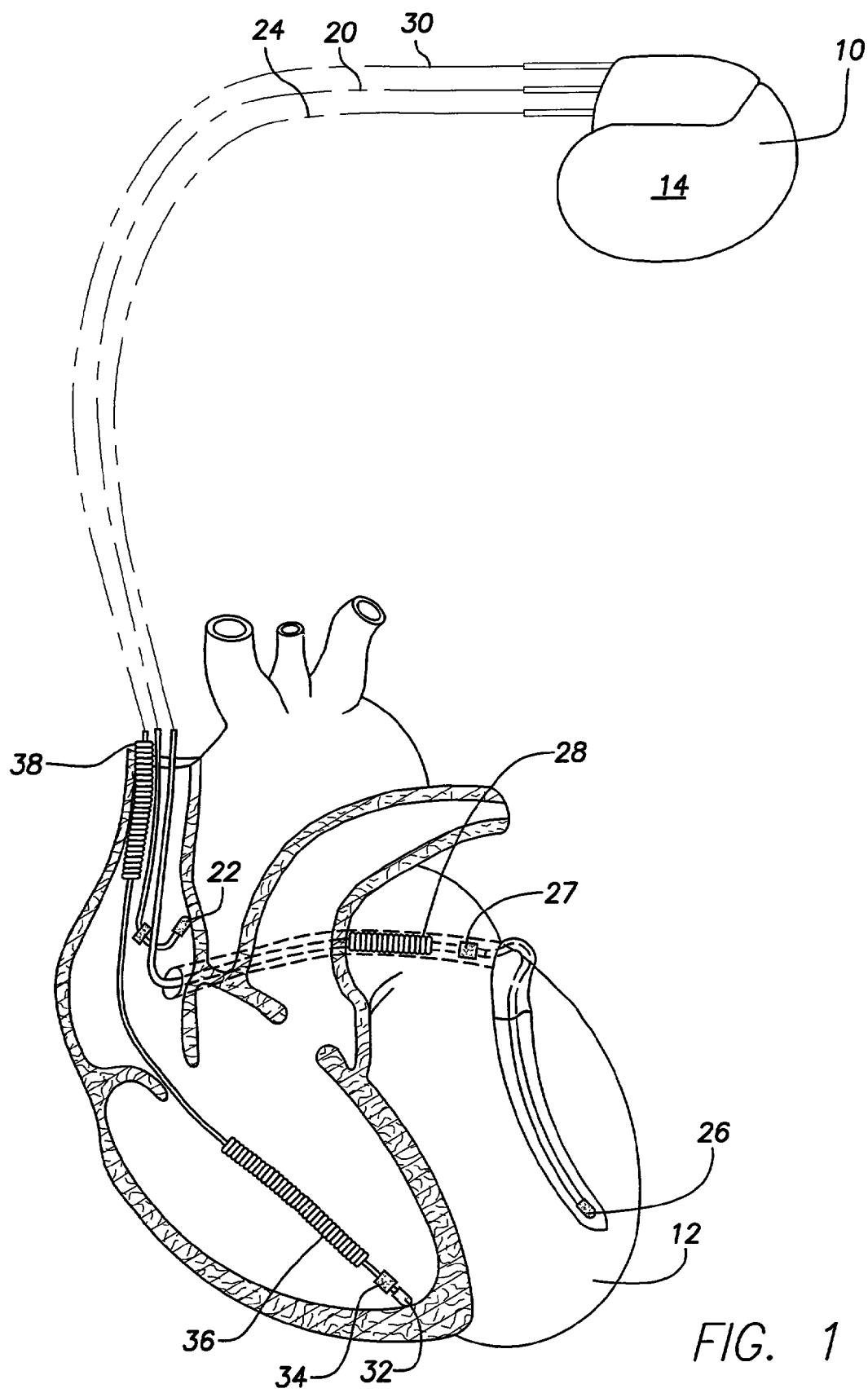
FIG. 1 is a diagrammatic elevation view, partly in section, of an implantable stimulation device of the type with which the present invention may be used.

As illustrated in FIG. 1, a simplified diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating an appropriate number of chamber(s) with cardioversion, defibrillation and pacing stimulation.

Briefly, as shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Accordingly, the right ventricular lead 30 is capable of receiving cardiac signals, and delivering stimulation in the form of pacing and shock therapy to the right ventricle.

While the complete details of a device that delivers multi-chamber stimulation and shock therapy is not salient to the invention, suffice it to say that the device requires low voltage and high voltage circuitry using a plurality of VLSI circuit chips and passive components. Thus, special attention is needed for conductors to be able to carry high voltage, high current pathways. For a complete description of an implantable stimulation device capable of pacing and sensing in two, three or four chambers and/or providing shock therapy, see U.S. application Ser. No. 09/930,725, entitled "Multi-site cardiac stimulation device for controlling Interchamber Delay" (Richard Lu) filed Aug. 14, 2001, which application is incorporated herein by reference.

Figure 2:
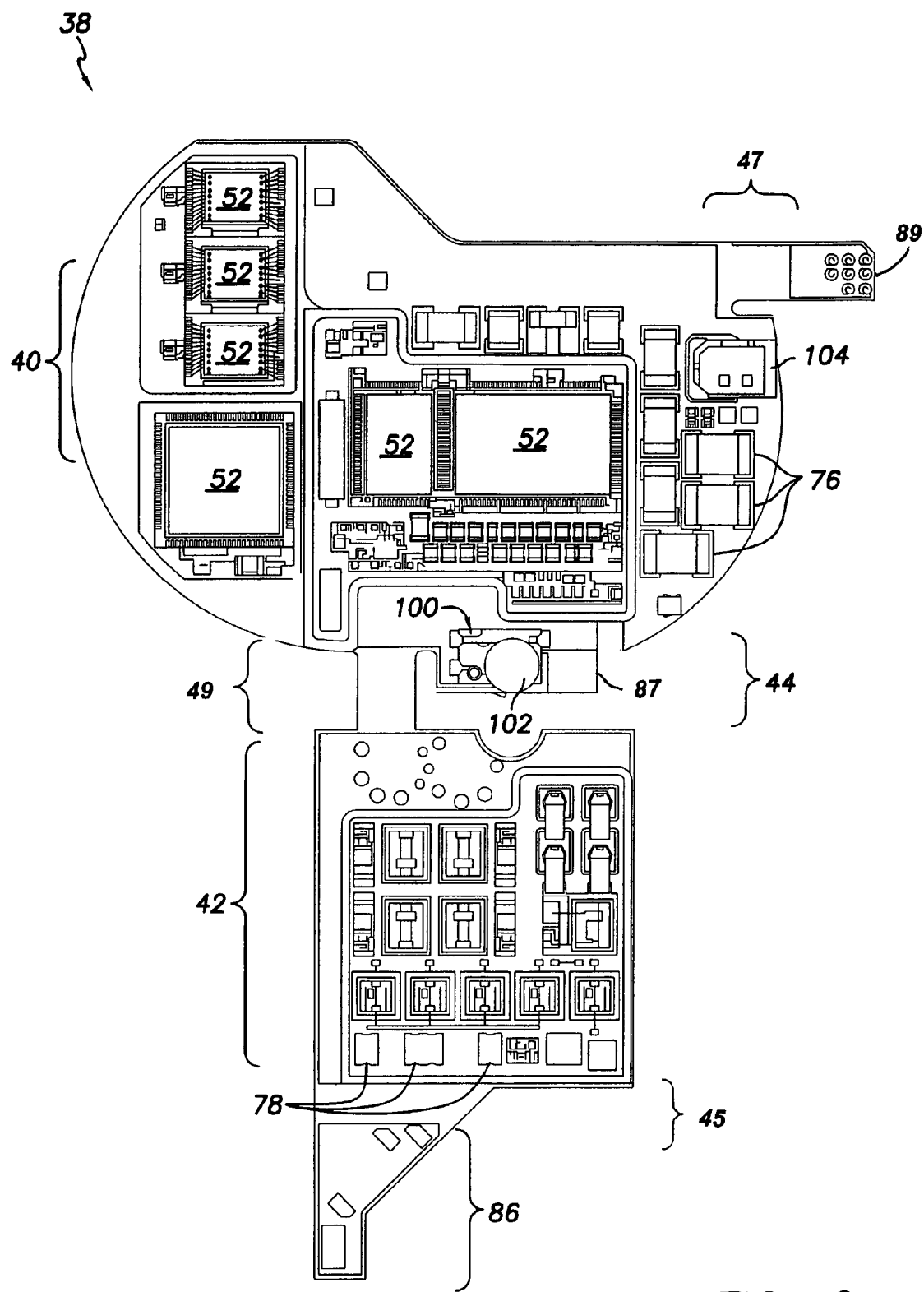
FIG. 2 is a diagrammatic top plan view of the component side of a flexible substrate on which is mounted a plurality of VLSI circuit chips as employed by the implantable stimulation device illustrated in FIG. 1.

As illustrated in FIG. 2, the stimulation device 10 includes a body compatible housing 14 which accommodates a flexible substrate 38 as the primary substrate for mounting number components into a high density microelectronic circuit. In this embodiment, the flexible substrate 38 has been partitioned into a low voltage assembly area 40 and a high voltage assembly area 42 to help improve isolation of the high voltage pathways and reduce crosstalk. The flexible substrate 38 is a high dielectric, flexible material, preferably polyimide. Unlike rigid substrates, the outline of the flexible substrate 38 can be adapted to conform to the body compatible housing 14.

As noted earlier, flexible polyimide exhibits a number of advantages including reduced thickness and weight as compared to conventional substrates, higher routing density, lower conductor resistance, and is capable of integrated interconnects in that polyimide substrates are flexible, such that interconnects can be designed into the substrates. When used as the primary substrate, no additional interconnect is needed for a battery connection, a capacitor connection, a telemetry coil connection, and a feedthrough connection since the flexible substrate can be configured to extend, reach and bend to meet these components. Furthermore, the flexible substrate has the ability to be folded one or more times (such as fold areas 44, 45, 47, and 49 in FIG. 2) to vertically integrate the substrate area with each fold, or otherwise conform to any shape defined by the outer housing of the implantable device.

The flexible substrate 38 is provided with a plurality of die attach pads 46 (see detail in FIG. 3), each of which has a plurality of wire bond pads 48 in close proximity to, or surrounding, each die attach pad 46. A plurality of chip-and-wire VLSI integrated circuit (IC) chips 52 (e.g., microprocessors, large scale RAM, ROM, and other custom IC's) are mounted on associated ones of the die attach pads 46 and each IC chip has a plurality of contact pads 74 formed on its top surface. Wire bonds 66 electrically connect the plurality of contact pads 74 to the wire bond pads 48. In each instance, the chip-and-wire integrated circuits 52 are mounted by epoxy or other suitable conductive adhesive material to the die attach pad on the flexible substrate 38. In a manner similar to that of the IC chips 52, a plurality of passive components (e.g., components 76 in area 40 and components 78 in area 42, FIG. 2) are mounted onto the flexible substrate 38 using conductive epoxy or other adhesive material. This epoxy attachment of the integrated circuits and passive components onto the flexible substrate is in contrast to known conventional techniques which employ solder reflow attachment of surface-mounted active and passive components onto flexible substrates.

Figure 3:
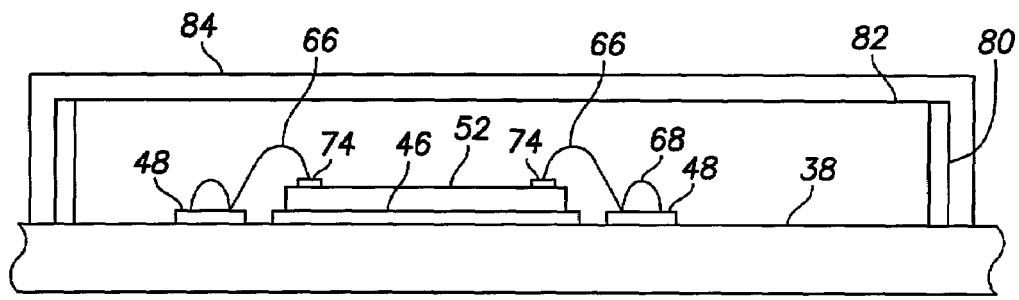
FIG. 3 is a cross section view of a VLSI circuit chip mounted on the flexible substrate and further illustrating safety bonds.

As further illustrated in FIG. 3, one or more IC chips 52 are encapsulated subsequent to the attachment of the wire bonds 66 using a non-conductive encapsulant (such as, Ablebond 7950 encapsulation from Ablestick, A National Starch and Chemical Company, Rancho Dominguez, Calif.). The encapsulation acts both as a moisture barrier, as an insulator (particularly if the substrate is folded), and as a protective cover during handling operations. The encapsulation may be accomplished by "glob topping" with non-conductive epoxy or, preferably, mounting a ring frame 80 around one or more IC chips and filling the ring frame 80 (FIG. 3) with non-conductive encapsulant 82. The use of the ring frame 80, advantageously, controls the height of the encapsulation. Optionally, the plurality of IC chips 52 may be protected with a conductive shield 84, which shield may be electrically connected to a known potential for shielding purposes.

In designing a substrate for an ICD, care should be taken in material selection and in partitioning the low voltage circuitry and output from the high voltage circuitry and outputs. Historically, separate substrates have been used to provide isolation to prevent cross talk and arcing between conductive traces. In the embodiment shown in FIG. 2, the majority of the low voltage circuitry (e.g., providing power to low voltage circuitry and pacing outputs) are located in area 40. The majority of the high voltage circuitry (e.g., the high voltage delivering output circuits, such as the Insulated Gate Bipolar Transistors (IGBTs)) are located in area 42 after the fold area 44. Since the conductors on the flexible substrate are copper, no additional PCB or interface is necessary. Accordingly, the flexible substrate 38 includes a feedthrough tab 86 that flexes to directly connect with the feedthroughs (not shown) in the housing 14. The flexible substrate 38 further includes a telemetry connection tab 87 and a battery connection tab 89.

We have found that material selection is important to achieve a reliable wire bond connection.

The prior art flex circuits have been known to use aluminum wire bonds. However, aluminum is not generally considered reliable enough for the numerous VLSI circuit chips that require the numerous (e.g., hundreds) of wire bonds in an ICD application, because of its lower fatigue strength. This is particularly important in view of the fact that the environment (the flexible substrate itself) will flex and bend. In ICD applications, the thicker aluminum wire bonds (e.g., 8 mil), which also have better fatigue performance due to its thickness, may be used on the high voltage output circuitry, but not on the VLSI circuit chips.

Gold wire bonds are preferred in high reliability applications for the VLSI circuit chips, such as implantable devices and space applications, because of its superior strength in fatigue applications and long history of reliability. However, gold wire bonds require more that the 1–3 micro-inches of immersion gold on the wire bond pads that was conventionally available on flex circuits. In fact, it was found that about 20 micro-inches was not sufficient to reliably adhere to the gold wire bonds.

Conventional electrolytic plating is not possible because of the complexity of the design precludes bus bars that are required for this process. Electroless chemistries commonly available have not yet been proven viable for this material set. Instead, it was discovered that with electrolytic pattern-plating of gold, the wire bond pads could achieve the required amount of gold, about 50 micro-inches (which is orders of magnitude greater than the standard 1–3 micro-inches available on conventional flex circuits), for this high reliability application.

It has been determined that gold and aluminum wire bonds can be used, depending on the application, in combination with a predetermined amount of gold plating on the wire bond pads.

More specifically, for low voltage applications, the wire bonds for the VLSI circuit chips should be about 1–1.25 mil gold wire (which is conventional in the chip-and-wire art) and the wire bond pads should have about 50 micro-inches of gold plating to achieve a reliable bond. The gold wire bonds include a primary bond 66 and may include a safety bond 68 to provide reinforcement of a bond tail on a substrate.

While not recommended for the VLSI circuit chips for the reasons stated above, some low voltage circuitry may alternatively use aluminum wire bonds of about 1–1.25 mil in diameter in combination with wire bond pads that have at least about 1–3 micro-inches of gold plating.

While the high voltage IGBT switches and conductors that need to pass high currents may use an 8 mil diameter aluminum wire in combination with wire bond pads that have at least about 1–3 micro-inches of gold plating, to simplify the manufacturing processing of the flexible substrate all of the wire bond pads may be processed uniformly across the substrate, i.e., to include about 50 micro-inches of gold plating. Alternatively, a plurality of 1–1.25 mil gold wires may be used for high current carrying outputs (e.g., 30 wires, or as needed by the current requirements). It is noted that the gates of each IGBT (which are low current inputs) only need to have about a 1–1.25 mil diameter gold or aluminum wire.

Figure 4:
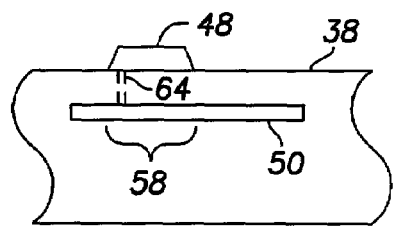
FIG. 4 is a cross section view of a flexible substrate illustrating reinforced wire bond pads.

As best seen in FIG. 4, each wire bond pad 48 is suitably connected to conductors 50 formed within the substrate according to circuit function. Such conductors are formed between successive layers of the substrate 38 by micro-vias 64.

It is recommend that each wire bond pad 48 preferably have an area of metallization 58 beneath the entire wire bond pad area to provide more structural support to minimize energy losses during the wire bonding process. It is noteworthy that the metallization layer 58 does not necessarily have to be the conductor that contacts the wire bond pad, but may be considered to be any conductor in the conductor layer immediately below the wire bond pad that provides structural support for the wire bond pad.

Figure 5:
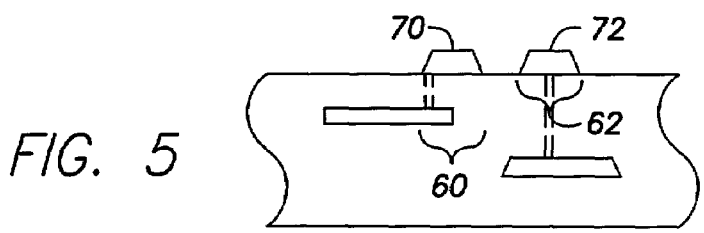
FIG. 5 is a cross section view of a flexible substrate illustrating unreinforced wire bond pads.

As shown in FIG. 5, areas 60 and 62 illustrate contact pads 70 and 72 that do not have an area of metallization beneath the entire wire bond pad area to provide more structural support. The absence of such metallization, in these instances, may be overcome using a special fixture to structurally support the flexible substrate 38 during wire bonding to minimize energy losses. A fixture that may be used to hold the flexible substrate 38 should include a porous metal base so that a uniform vacuum hold down can be exerted on the flexible substrate 38 so as to avoid deforming the bonding surfaces during automatic bonding. This would be in contrast with a conventional fixture which has multiple vacuum holes and may deform the flexible substrate during wire bonding.

As shown in FIG. 2, and using the recommendations outlined above, hundreds of gold wire bonds may be electrically connected to the plurality of contact pads on top of each VLSI circuit chip to the wire bond pads on the flexible substrate. As such, the wire bonds may be placed using conventional automatic wire bonding equipment and the fixture described above, such as, a KME Wire Bonder, such as the HW27U-H Wire Bonder available from Kyushu Matsushita Electric, Co., a division of Panasonic of Fukuoka, Japan.

As best seen in FIG. 2, a daughterboard 100 for adding other components, such as the telemetry coil 102, may be mounted, typically by epoxy, onto the flexible substrate 38. An accelerometer 104, or other sensor, may also be attached as a subassembly onto the flexible substrate. If desired, the accelerometer 104, or other daughterboard, could be mounted perpendicular to the flexible substrate with interconnecting tabs folding to mate with the accelerometer, or daughterboard. These examples are presented to illustrate the flexibility of a flexible substrate as the primary substrate to conform to any configuration needed to meet the requirements of an implantable device.

Figure 6:
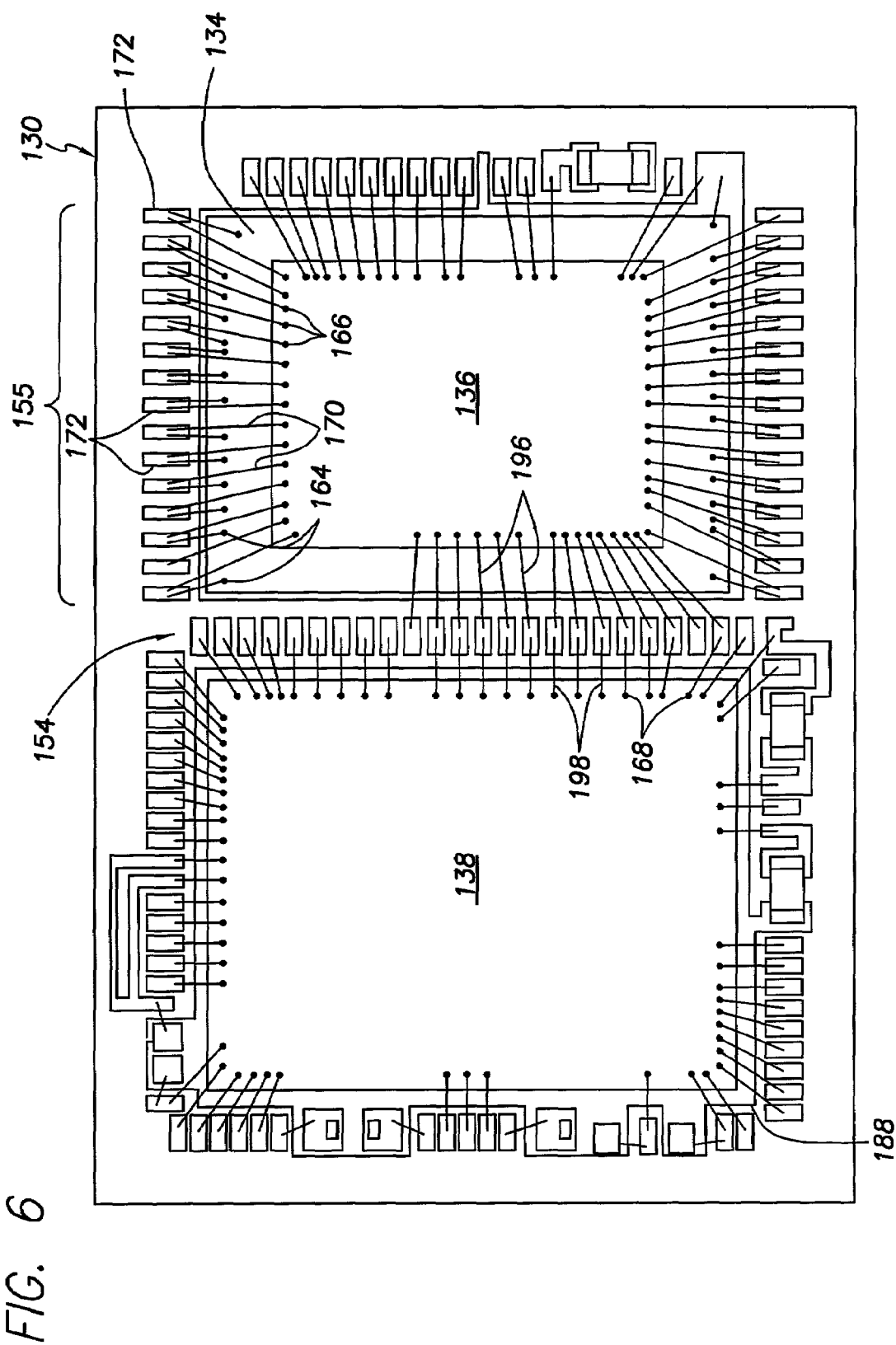
FIG. 6 is a plan view of the two vertically stacked chip-and-wire mounted IC's that may be used in an alternative embodiment.

FIG. 6 illustrates an additional feature or embodiment that is enabled by the present invention, which is a "die-on-die" arrangement that is mounted onto a flexible substrate 130. In conventional chip-and-wire layouts, a substantial portion of the substrate surface is occupied by components. To further improve packaging density, the VLSI circuit chips 134, 136 and 138, are interconnected with the flexible substrate 130 in a manner which minimizes the required size of the flexible substrate 130 by vertically stacking the chips 136 onto 138. Specifically, the integrated circuits 134, 136, and 138 each contain multiple contact pads 164, 166, and 168, respectively that are, in turn, connected to wire bond pads placed on the surface of the flexible substrate 130. For example, the row of wire bond pads 155 are individually connected to the contact pads 164 through wire bonds 172. The same individual wire bond pads are also connected to the contact pads 166 through wire bonds 170.

In the preferred embodiment, the contact pads 164 on chip 134 and contact pads 166 on chip 136 form a set of unique pairs of contact pads wherein each pair, while not directly connected together, are in electrical communication through mutual contact, via wire bonds 170 and 172, with a corresponding wire bond pad from the row of wire bond pads 155. This paired connection scheme could be continued along all four edges of the chip 134. It can be appreciated, however, that not all wire bond pads along the rows need be "shared" with contact pads from both of the chips 134 and 136. The exact number of wire bond pads which are shared will depend upon a specific design.

Optimally, the layout of the flexible substrate, i.e., the position of all of the components and their interconnecting pathways, will result in a maximum number of wire bond pads being "shared" by connection to two or more components. Such optimization of the layout can be more easily achieved if the chips 134 and 136 themselves can be engineered for a specific application whereby the contact pads are strategically placed. However, even using standard integrated circuit chips, the packaging density of a circuit application can be significantly increased by implementing the concepts of the claimed invention. Such an increase in packaging density through use of shared wire bond pads also significantly reduces noise within the circuit structure.

Figure 7:
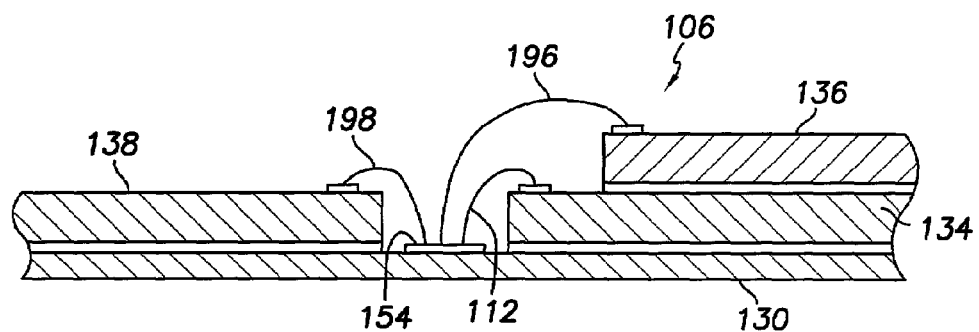
FIG. 7 is an elevation view of an alternative embodiment wherein wire bond pads are shared by three IC's.

To further increase packaging density, the third integrated circuit 138 is placed on the flexible substrate 130 within a die-attach pad 188 which is adjacent to the vertically-stacked chips 134 and 136. Individual wire bond pads from the row of wire bond pads 154 are selectively connected to either one or both of the chips 136 and 138 through wire bonds 196 and 198, respectively. As shown in FIG. 7, a row of wire bond pads may be shared by three IC chips 134, 136 and 138 through wire bonds 196, 198 and 112. Use of this configuration will again depend on the specific application of the vertically integrated package.

Figure 8:
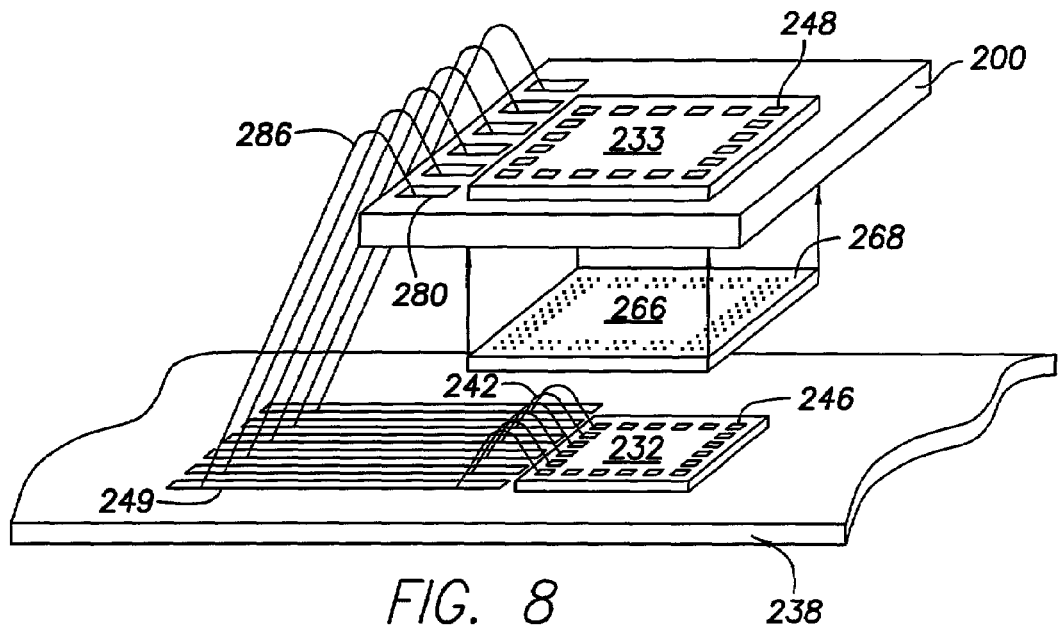
FIG. 8 shows a partial exploded view of another embodiment of the present invention having three stacked chip-and-wire mounted IC's.
Figure 9:
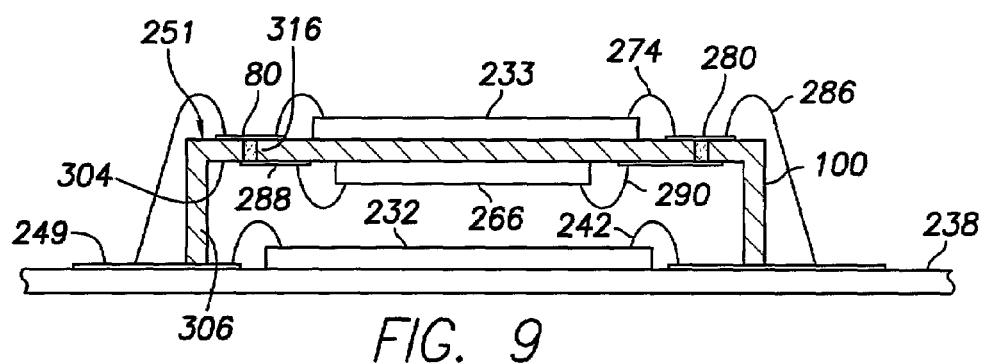
FIG. 9 shows a side view of the vertically integrated electronic package shown in FIG. 8.

In another alternate embodiment shown in FIGS. 8 and 9, the vertical integration of two or more chip-and-wire VLSI chips onto a flexible substrate 238 is achieved by a lid, or cover, 200 which includes two surfaces for mounting components: the exterior, top surface 251 and an interior, bottom surface 304 within a cavity 306. The chip 233 is mounted on the top surface 251 with the chip 266 mounted on the bottom surface 304. The lid 200 includes intermediate conductors 280 and 288 around the periphery of the chips 233 and 266, respectively. Interconnection between the pairs of intermediate conductors 280 and 288 occurs using metallized vias 316, or equivalent, formed within the lid 200. The second and third contact pads 248 and 268 of the chips 233 and 266 are electrically connected to the intermediate conductors 280 and 288 using a plurality of wire bonds 274 and 290, respectively.

Preferably, the plurality of first, second and third contact pads 246, 248 and 268 are positioned to define unique triads of contact pads, each triad comprising a contact pad from the plurality of first contact pads 246, a contact pad from the plurality of second contact pads 248, and a contact pad from the plurality of third contact pads 268. A plurality of metallized bond fingers 249 are in electrical contact with a respective one of the plurality of second and third contact pads 248 and 268, respectively, through the plurality of wire bonds 274, 286 and the intermediate conductors 280. The plurality of metallized bond fingers 249 are further in electrical contact with a respective one of the first contact pads 246 through the plurality of wire bonds 242. (For simplicity, the wire bonds are only shown on one side, but it is understood that the wire bonds may be used on all four sides of the chips 232, 233 and 266.) Thus, the plurality of metallized bond fingers 249 electrically connect together each contact pad of each triad of contact pads.

While not shown in any of FIGS. 6–9, safety bonds could be employed in any of the paired wire bonds for additional reinforcement.

Advantageously, the packaging density has been increased to include another component (chip 266) without significantly adding to the thickness of the overall package. Furthermore, it is recognized that passive components associated with the chips 233 and 266 can be mounted onto or under the lid to further simplify the interconnection between the devices.

In the preferred embodiment, the chips 233 and 266 also have similar pad-outs so that unique pairs of contact pads are vertically disposed. Advantageously, this configuration enables the lid 200 to be a single layer of ceramic, with a simple metallization pattern on both surfaces 251 and 304.

It will therefore be perceived that the advantages of the combination of a flexible substrate with chip-and-wire can be achieved on complex, high voltage and low voltage VLSI circuits employed in ICD's. Furthermore, this achievement results in a significant weight and size reduction of the ICD while accommodating complex functionality, and further affording expandability through the ability to stack additional RAM and/or ROM IC's, thereby making the method of the present invention a highly desirable enhancement to implantable cardioverter-defibrillator therapy. While the present invention was motivated by the needs of an ICD device, and its high voltage requirements, it is apparent that these techniques may be applied to reduce the size and enhance manufacturability of other implantable medical devices, such as pacemakers, hearing aids, infusion pumps, etc.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. In an implantable medical device, a high density microelectronic package, comprising:
    a primary substrate made of thin, highly flexible and foldable, high dielectric strength material, the primary substrate having a top side and a bottom side with a plurality of conductive and non-conductive interconnect layers therebetween, the primary substrate having die attach pads on the top side, each die attach pad having a plurality of wire bond pads therearound, each wire bond pad being connected to the conductive interconnect layers according to circuit function;
    a plurality of chip-and-wire VLSI circuit chips mounted on the die attach pads, each VLSI circuit chip have a plurality of contact pads formed on a top surface thereof; and
    a plurality of gold wire bonds that electrically connect the plurality of contact pads to a respective wire bond pad;
    wherein each of the wire bond pads has about 50 micro-inches of gold plating thereon; and
    wherein the primary substrate comprises a fold area and wherein the primary substrate is adapted to be folded at the fold area to vertically integrate the primary substrate; and
    wherein the primary substrate comprises a first assembly area and a second assembly area, wherein the primary substrate is folded at the fold area to vertically integrate the first assembly area with the second assembly area, and wherein the first assembly area is connected with the second assembly area only at the fold area.

2. The high density microelectronic circuit, as recited in claim 1, wherein:
    the plurality of gold wire bonds for the plurality of contact pads are gold wire bonds at least 0.001 inches in diameter.

3. The high density microelectronic circuit, as recited in claim 2, wherein the gold wire bonds are reinforced with a safety bond.

4. The high density microelectronic circuit, as recited in claim 1, further comprising:
    high voltage circuitry that are interconnected using high current carrying conductors; and
    aluminum wire bonds for connecting the high voltage circuitry to the high current carrying conductors, the aluminum wire bonds comprising at least 0.008 inches in diameter.

5. The high density microelectronic circuit, as recited in claim 1, wherein the plurality of chip-and-wire VLSI circuit chips are encapsulated subsequent to the attachment of the wire bonds with non-conductive epoxy, thereby protecting the integrated circuit chips and making the flexible substrate rigid.

6. The high density microelectronic circuit, as recited in claim 5, wherein the plurality of chip-and-wire VLSI integrated circuit chips are encapsulated with non-conductive epoxy within a ring frame, wherein the ring frame controls the height and area of the encapsulation.

7. The high density microelectronic circuit, as recited in claim 1, wherein at least two of the plurality of the VLSI circuit chips share wire bond pads to increase packaging density.

8. The high density microelectronic circuit, as recited in claim 1, wherein at least two of the plurality of the VLSI circuit chips are stacked in with a similar pad-out so that wire bond pads are shared so as to increase packaging density.

9. The high density microelectronic circuit, as recited in claim 8, wherein the at least two stacked VLSI circuit chips are mounted using a die-on-die configuration so as to further increase packaging density.

10. The high density microelectronic circuit, as recited in claim 1, wherein the flexible substrate further comprises additional components on the bottom side.

11. The high density microelectronic circuit, as recited in claim 1, wherein the flexible substrate comprises folded connection tabs that conform to external components including at least one of a battery connection tab, a telemetry connection tab, and a feedthrough tab.

12. The high density microelectronic circuit, as recited in claim 11, wherein the daughterboard can be mounted planar or perpendicular onto the flexible substrate, the flexible substrate further comprising a connection tab that can be folded to mate to the daughterboard.

13. The high density microelectronic circuit, as recited in claim 1, further comprising a daughterboard mounted onto the flexible substrate.

14. The high density microelectronic circuit, as recited in claim 1, wherein the primary substrate comprises a low voltage assembly area and a high voltage assembly area, and wherein the primary substrate is folded at the fold area to vertically integrate the low voltage assembly area with the high voltage assembly area.

15. The high density microelectronic circuit, as recited in claim 1, wherein the first assembly area has a first side and the second assembly area has a second side, wherein the first side is in opposition with the second side, and wherein the first assembly area and the second assembly area are parallel and spaced from one another so as to define a space between the first side and the second side.

16. In an implantable medical device, a high density microelectronic package, comprising:
    a primary substrate made of thin, highly flexible and foldable, high dielectric strength material, the primary substrate having a top side and a bottom side with a plurality of conductive and non-conductive interconnect layers therebetween, the primary substrate having die attach pads on the top side, each die attach pad having a plurality of wire bond pads therearound, each wire bond pad being connected to the conductive interconnect layers according to circuit function;

a plurality of chip-and-wire VLSI circuit chips mounted on the die attach pads, each VLSI circuit chip have a plurality of contact pads formed on a top surface thereof;

a plurality of gold wire bonds that electrically connect the plurality of contact pads to a respective wire bond pad; and a predetermined amount of electrolytic pattern-plated gold on each of the VLSI wire bond pads, the predetermined amount being sufficient to ensure adherence with the gold wire bonds;

wherein the primary substrate comprises a fold area and wherein the primary substrate is adapted to be folded at the fold area to vertically integrate the primary substrate; and wherein the primary substrate comprises a first assembly area and a second assembly area, and wherein the primary substrate is folded at the fold area to vertically integrate the first assembly area with the second assembly area, and wherein the first assembly area is connected with the second assembly area only at the fold area.

17. The high density microelectronic package, as recited in claim 16, wherein the primary substrate comprises a low voltage assembly area and a high voltage assembly area, and wherein the primary substrate is folded at the fold area to vertically integrate the low voltage assembly area with the high voltage assembly area.

18. The high density microelectronic package, as recited in claim 16, wherein the primary substrate comprises folded connection tabs that conform to external components including at least one of a battery connection tab, a telemetry connection tab, and a feedthrough tab.

19. The high density microelectronic package, as recited in claim 18, further comprising a daughterboard mounted onto the flexible substrate.

20. The high density microelectronic circuit, as recited in claim 16, wherein the first assembly area has a first side and the second assembly area has a second side, wherein the first side is in opposition with the second side, and wherein the first assembly area and the second assembly area are parallel and spaced from one another so as to define a space between the first side and the second side.

* * * * *